United States Patent
Devisetty

(10) Patent No.: US 9,854,797 B2
(45) Date of Patent: Jan. 2, 2018

(54) GIBBERELLIN GRANULAR FORMULATIONS

(71) Applicant: Valent BioSciences Corporation, Libertyville, IL (US)

(72) Inventor: Bala N. Devisetty, Buffalo Grove, IL (US)

(73) Assignee: VALENT BIOSCIENCES CORPORATION, Libertyville, IL (US)

( * ) Notice: Subject to any disclaimer, the term of this patent is extended or adjusted under 35 U.S.C. 154(b) by 0 days.

(21) Appl. No.: 15/371,402

(22) Filed: Dec. 7, 2016

(65) Prior Publication Data

US 2017/0156316 A1    Jun. 8, 2017

Related U.S. Application Data

(60) Provisional application No. 62/263,822, filed on Dec. 7, 2015, provisional application No. 62/424,631, filed on Nov. 21, 2016, provisional application No. 62/426,818, filed on Nov. 28, 2016.

(51) Int. Cl.
| | |
|---|---|
| *A01N 25/30* | (2006.01) |
| *A01N 43/12* | (2006.01) |
| *A01N 25/12* | (2006.01) |

(52) U.S. Cl.
CPC .................................... *A01N 25/12* (2013.01)

(58) Field of Classification Search
CPC ................................ A01N 43/12; A01N 25/30
See application file for complete search history.

(56) References Cited

U.S. PATENT DOCUMENTS

| | | | |
|---|---|---|---|
| 2003/0008949 A1 | 1/2003 | Devisetty et al. | |
| 2013/0225410 A1* | 8/2013 | Haas ....................... | A01N 43/82 504/272 |
| 2015/0080216 A1* | 3/2015 | Wikeley ................. | A01N 43/08 504/136 |
| 2015/0173365 A1* | 6/2015 | Devisetty ............... | A01N 43/12 504/297 |

OTHER PUBLICATIONS

International Search Report and Written Opinion issued by the International Bureau in corresponding application No. PCT/US2016/065266 dated Feb. 17, 2017.

* cited by examiner

*Primary Examiner* — Johann R Richter
*Assistant Examiner* — Genevieve S Alley
(74) *Attorney, Agent, or Firm* — Wood, Phillips, Katz, Clark & Mortimer

(57) ABSTRACT

The present invention relates to granular gibberellin formulations and methods of their use.

20 Claims, No Drawings

GIBBERELLIN GRANULAR FORMULATIONS

FIELD OF THE INVENTION

The present invention relates to gibberellin granular formulations.

BACKGROUND OF THE INVENTION

Gibberellins are a class of plant growth regulators which are diterpenoid acids. Gibberellins are commercially produced by fermentation of a natural fungus, *Gibberella fugikuroi*. Gibberellins are marketed under various trade names and are commercially used on a variety of fruit orchards, vegetable crops, row crops, and ornamental crops. The predominantly used gibberellin is gibberellin acid ("$GA_3$").

Currently there is a strong need for methods to effectively and conveniently deliver gibberellins to the root systems of plants. Further, it is desirable to be able to deliver the gibberellin to the root system even when the root system is under standing water. An effective soil application would be desirable because it places the gibberellin in close proximity to the root system which can then efficiently uptake the gibberellin.

One issue with soil application is that when prior art formulations, such as powders, are applied to flooded crop growing areas, the gibberellin might remain on the surface of the water due to its poor wetting and low water solubility. The gibberellin might then break down due to hydrolysis before the plants' roots can absorb it.

Clay-based formulations have been used in attempts to deliver the gibberellin to the plants, as well. This method failed because the clay granules did not deliver or release the gibberellin to the soil. Further, clay based products tend to produce dust upon handling, such as when pouring, transferring or measuring them. This dust may pose health hazards.

A further issue is that it is desirable to apply low concentrations of gibberellins to flooded crop plants. Such low levels of gibberellins require large amounts of excipients or carriers which can leave residues on the plants or growing environment. In addition, the excipients or carriers could greatly increase the cost of the gibberellin product due to excessive processing and transportation costs.

Therefore, there is a need for environmentally safe, non-phytotoxic, efficacious, and economic gibberellin formulations which can be applied to the soil, including when the soil is under standing water. The improved formulations should overcome the toxicity, handling, storage, transportation, and delivery issues encountered by prior art formulations.

SUMMARY OF THE INVENTION

In one aspect, the present invention is directed to granular formulations comprising from about 0.01 to about 1% wt/wt of at least one gibberellin selected from the group consisting of $GA_3$, gibberellin 4 ("$GA_4$"), gibberellin 7 ("$GA_7$") and gibberellin 4/7 ("$GA_{4/7}$"), from about 0.1 to about 1% wt/wt of at least one solvent selected from the group consisting of polyethylene glycols with average molecular weights of from about 190 to about 420 daltons and C8 to C12 fatty acid dimethylamides, from about 0.0001 to about 0.1% wt/wt of a binder, from about 0.0001 to about 0.1% wt/wt of a non-ionic surfactant, from about 0.01 to about 2% wt/wt of a free-flow agent, and from about 97 to about 99.9% wt/wt of sand granules with average diameters of from about 0.05 to about 2 mm.

In a further aspect, the present invention is directed to agricultural granular formulations comprising from about 0.01 to about 1% wt/wt of $GA_3$, from about 0.1 to about 1% wt/wt of at least one solvent selected from the group consisting of polyethylene glycols with average molecular weights of from about 190 to about 420 daltons and C8 to C12 fatty acid dimethylamides, from about 0.0001 to about 0.1% wt/wt of a copolymer of acetic acid ethenyl ester and 1-ethenyl-2-pyrrolidinone, from about 0.0001 to about 0.1% wt/wt of a non-ionic surfactant selected from the group consisting of polyoxyethylene (20) sorbitan monolaurate and polyoxyethylene (20) sorbitan monooleate, from about 0.01 to about 2% wt/wt of sodium aluminosilicate, and from about 97 to about 99.9% wt/wt of silica sand granules with average diameters of from about 0.6 to about 1.4 mm.

In another aspect, the present invention is directed to methods for regulating plant growth comprising treating a plant or plant growing environment with an effective amount of the formulations of the present invention.

DETAILED DESCRIPTION OF THE INVENTION

Applicant has unexpectedly discovered gibberellin granular formulations that are easy to apply and are stable, safe, and effective soil treatments. Using sand as a carrier in the formulation makes the formulations suitable to be applied to soil covered by standing water because the sand is heavy and allows the granular formulation to quickly sink in the water to effectively reach the soil. Sand is also nontoxic and does not form residues. Further, Applicant found that sand granules applied to the soil surrounding plants was an effective treatment because the adjacent plants were capable of absorbing the gibberellins very efficiently.

A further advantage of the present invention is that the pre-mixture formulation that is first applied to the sand granules is sticky which allows for additional gibberellin to be applied to the granule. The resulting sand granules are the proper texture, free flowing and are non-sticky or dusty.

Another advantage of the present invention is that sand can be sourced from the areas in need of gibberellin treatment which results in significant savings in transportation costs. For example, there is a great need in India for gibberellin application in paddy fields (rice) and sand is not cost prohibitive and it can be widely sourced in India.

The formulations can be applied directly or by combining with various granular fertilizers. This provides the growers with greatly needed flexibility.

In one embodiment, the present invention is directed to granular formulations comprising from about 0.01 to about 1% wt/wt of at least one gibberellin selected from the group consisting of $GA_3$, $GA_4$, $GA_7$ and $GA_{4/7}$, from about 0.1 to about 1% wt/wt of at least one solvent selected from the group consisting of polyethylene glycols with average molecular weights of from about 190 to about 420 daltons and C8 to C12 fatty acid dimethylamides, from about 0.0001 to about 0.1% wt/wt of a binder, from about 0.0001 to about 0.1% wt/wt of a non-ionic surfactant, from about 0.01 to about 2% wt/wt of a free-flow agent, and from about 97 to about 99.9% wt/wt of sand granules with average diameters of from about 0.05 to about 2 mm.

In a preferred embodiment, the gibberellin is $GA_3$.

In another embodiment, the formulation comprises from about 0.01 to about 1% wt/wt of at least one gibberellin. In a preferred embodiment, the formulations comprise from about 0.05 to about 0.3% wt/wt of at least one gibberellin. In a most preferred embodiment, the formulations comprise about 0.1 to about 0.2% wt/wt of at least one gibberellin.

In a further embodiment, the formulations comprise from about 0.005 to about 0.1% wt/wt of a color additive. In a preferred embodiment, the color additive is a dye. In a more preferred embodiment, the dye is a FD&C food grade dye. In an even more preferred embodiment, the dye is selected from the group consisting of FD&C Blue #1, FD&C Blue #2, FD&C Green #3, FD&C Red #3, FD&C Red #40, FD&C Yellow #5, FD&C Yellow #6, and Citrus Red #2. In a most preferred embodiment, the dye is FD&C Blue #1. In another most preferred embodiment, the dye is FD&C Red #40.

As used herein, "FD&C" refers to the United States' Food, Drug, and Cosmetic Act which is United States Code, Title 21. This code provides the following list (as of October 2015) of food grade color additives which may be added to foods: FD&C Blue #1; FD&C Blue #2; FD&C Green #3; FD&C Red #3; FD&C Red #40; FD&C Yellow #5; FD&C Yellow #6; and Citrus Red #2.

Polyethylene glycol ("PEG") is a polyether compound with the structure: H—(O—CH$_2$—CH$_2$)$_n$—OH. PEGs are prepared by polymerization of ethylene oxide and are commercially available over a wide range of molecular weights. The number following "polyethylene glycol", or "PEG", refers to the molecular weight. For example, PEG 200 has a range of molecular weights from 190 to 210, PEG 300 from 285 to 315, and PEG 400 from 380 to 420 daltons. In a preferred embodiment, the solvent is polyethylene glycols with average molecular weights of from about 190 to about 420 daltons. In a more preferred embodiment, the solvent is polyethylene glycols with average molecular weights of from about 190 to about 210 daltons.

In another embodiment, the solvent is at least one C8 to C12 fatty acid dimethylamide. In a preferred embodiment, the solvent is a mixture of C8 to C10 fatty acid dimethylamides or a mixture of C10 to C12 fatty acid dimethylamides. In a more preferred embodiment, the solvent is a mixture of C8 to C10 fatty acid dimethylamides. A mixture of C8 to C10 fatty acid dimethylamides is commercially available as Agnique® AMD 810 (Agnique is available from BASF and a registered trademark of Cognis Corporation).

In a further embodiment, the solvent is a mixture of: (1) polyethylene glycols with average molecular weights of from about 190 to about 210 daltons; and (2) a mixture of C8 to C10 fatty acid dimethylamides.

In an embodiment, the binder is selected from the group consisting of polyvinyl pyrrolidone, a lignosulfonate, a lignin, a lecithin, a starch, a gluten, a polyethylene glycol, a disaccharide, hydrolyzed starch, a sugar alcohol, polyvinyl alcohols, celluloses, alkylated vinyl pyrrolidone polymers, a copolymer of acetic acid ethenyl ester and 1-ethenyl-2-pyrrolidinone, a copolymer of polyvinylpyrrolidone and 1-eicodecene, and combinations thereof. In an embodiment, the disaccharide is selected from the group consisting of sucrose, lactose, and maltose. In an embodiment, the hydrolyzed starch is selected from the group consisting of maltodextrin and corn syrup solids. In an embodiment, the sugar alcohol is selected from the group consisting of sorbitol and mannitol. In another embodiment, the polyvinyl alcohol is hydrolyzed.

In a preferred embodiment, the binder is a copolymer of acetic acid ethenyl ester and 1-ethenyl-2-pyrrolidinone (vinyl pyrrolidone/vinyl acetate copolymer, available from Ashland as Agrimer™ VA-6). Alklated vinyl pyrrolidone polymers, such as Agrimer™ AL10, and a copolymer of polyvinylpyrrolidone and 1-eicodecene, Agrimer™ VA-30, are also available from Ashland.

In a further embodiment, the formulations comprise from about 0.0001 to about 0.1% wt/wt of the binder. In a preferred embodiment, the formulations comprise from about 0.005 to about 0.1% wt/wt of the binder. In a more preferred embodiment, the formulations comprise about 0.01% wt/wt of the binder.

In another embodiment, the non-ionic surfactant is selected from the group consisting of polyoxyethylene (20) sorbitan monolaurate and polyoxyethylene (20) sorbitan monooleate. In a preferred embodiment, the non-ionic surfactant is polyoxyethylene (20) sorbitan monolaurate.

In an embodiment, the formulations comprise from about 0.0001 to about 0.1% wt/wt of the non-ionic surfactant. In a preferred embodiment, the formulations comprise from about 0.001 to about 0.1% wt/wt of the non-ionic surfactant. In a more preferred embodiment, the formulations comprise about 0.006% wt/wt of the non-ionic surfactant.

In an embodiment, the sand is selected from the group consisting of silica sand, volcanic sand, mineral sand, biogenic sand, and lithic sand. In a preferred embodiment, the sand is silica sand.

In a further embodiment, the formulations comprise from about 97 to about 99.9% wt/wt of sand. In a preferred embodiment, the formulations comprise from about 97.5 to about 99.5% wt/wt of sand. In a more preferred embodiment, the formulations comprise about 99% wt/wt of sand.

In an embodiment, the sand has average particle diameters of from about 0.05 to about 2 mm. In a preferred embodiment, the sand has average particle diameters of from about 0.6 to about 1.4 mm.

In an embodiment, the free-flow agent is selected from the group consisting of sodium aluminosilicate, silicon dioxide, calcium carbonate, and magnesium carbonate. In a preferred embodiment, the free-flow agent is sodium aluminosilicate.

In a further embodiment, the formulations comprise from about 0.01 to about 2% wt/wt of the free flow agent. In a preferred embodiment, the formulations comprise from about 0.1 to about 1.0% wt/wt of the free flow agent. In a more preferred embodiment, the formulations comprise about 0.5% wt/wt of the free flow agent.

In yet another embodiment, the present invention is directed to methods for regulating plant growth comprising treating a plant or plant growing environment with an effective amount of a formulation of the present invention.

The formulations of the present invention are also low VOC formulations. This means that the formulations contain less than or equal to 25% emission potential, as determined by thermo gravimetric analysis ("TGA"). Gibberellin formulations with greater than 25% emission potential, as determined by TGA, are considered High-VOC products by CADPR (California Department of Pesticide Regulation). TGA involves heating a sample of the formulation in an environmentally controlled chamber while the rate of sample mass loss is measured. CADPR states that the emission potential of the formulation is determined by taking the mean of three replicate TGA measurements of the formulations and then subtracting the percent water and the exempt compounds from the measurement. The TGA process is well known by those of skill in the art.

In a further embodiment, the formulations of the present invention are applied to plants or a plant growing environment at a rate of from about 0.01 to about 30 grams of gibberellin per hectare. In a preferred embodiment, the formulations are applied to the plants or a plant growing environment at a rate of from about 0.01 to about 5 grams of gibberellin per hectare. In a more preferred embodiment, the formulations are applied to the plants or plant growing environment at a rate of from about 0.01 to about 2 grams of gibberellin per hectare. In another preferred embodiment, the formulations are applied to the plants or a plant growing environment at a rate of from about 10 to about 25 grams per hectare and more preferably from about 12.5 to about 25 grams per hectare and even more preferably about 12.5 or about 25 grams per hectare.

Formulations of the present invention may be used on any plant in need of gibberellin treatment (or on the plant growing environment (such as soil) adjacent to the plant in need of treatment), for example, on: artichokes to accelerate maturity and increase yield; blueberries to improve fruit set and fruit size; bananas to stimulate plant growth and reduce effects of stress, or post-harvest for maintaining fruit quality; carrots to maintain foliage growth during periods of stress; celery to increase plant height and yield; cherries to increase fruit size, firmness and quality or to delay maturity for a more orderly harvest; citrus to increase fruit set and yield, to delay rind aging, reduce physiological disorders, or delay maturity for a more orderly harvest; collard greens to facilitate harvest, increase yield, and improve quality; cotton to promote early season growth and increase seedling vigor; and cucumbers to stimulate fruit set during periods of cool weather; pasture land used for animal grazing; and corn. The formulations can be used post harvest on bananas and citrus, etc. Formulations of the present invention could also be used on grapes, melons, pecans, peppers, pineapples, rice, rhubarb, spinach, stone fruits, sugarcane, wheat, strawberries, watercress and other plants in need of treatment.

In an embodiment, the formulations of the present invention are applied to a plant selected from the group consisting of rice, cotton, corn, soybeans, sugarcane, wheat and beets. In a preferred embodiment, the formulations of the present invention are applied to a plant selected from the group consisting of rice, corn and wheat.

In a further embodiment, the formulations of the present invention are applied to a plant growing environment where rice, cotton, corn, soybeans, sugarcane, wheat and/or beets are growing. In a preferred embodiment, the formulations of the present invention are applied to a plant growing environment where rice, corn or wheat is growing.

The disclosed embodiments are simply exemplary embodiments of the inventive concepts disclosed herein and should not be considered as limiting, unless the claims expressly state otherwise.

The term "effective amount" means the amount of the formulation that will provide the desired effect on the plant that is being treated. The "effective amount" will vary depending on the formulation concentration, the type of plants(s) being treated, and the result desired, among other factors. Thus, it is not always possible to specify an exact "effective amount." However, an appropriate "effective amount" in any individual case may be determined by one of ordinary skill in the art. For example, effective amounts of formulations of the present invention may be from about 0.1 to about 10 grams of gibberellin per hectare.

Other components of the formulation may be included in nominal amounts that do not affect the storage stability and performance characteristics of the present formulations. Additional components include additional surface active agents, crystal growth inhibitors, stickers, spreaders, leaf penetrants, dispersants, systemic acquired resistance inducers, systemic acquired resistance inhibiters, biostimulants, seed inoculants, bionematicides, biofungicides, insecticides and fungicides, anti-foaming agents, preservatives, pH regulators, cosolvents, humectants, UV protectants, vehicles, sequestrants or other components which facilitate production, storage stability, product handling and application.

It is also contemplated that the formulation of this invention may be used in combination with other active ingredients, such as herbicides, fungicides, insecticides, bactericides, nematicides, biochemical pesticides, plant produced pesticides (botanicals), safeners or plant nutrients.

As used herein, the term "herbicide" broadly refers to compounds or compositions that are used as herbicides, as well as herbicide safeners and algicides. Herbicides may include, but are not limited to, 1,2,4-triazinones, 1,3,5-triazines, alkanamides (acetamides), anilides, aryloxyalkanoic acids, aryloxyphenoxypropionates, benzamides, benzamides (L), benzenedicarboxylic acids, benzofurans, benzoic acids (auxins), benzonitriles, benzothiadiazinones, benzothiazolones, carbamates (DHP), carbamates, chloroacetamides, cyclohexanedione oximes, dinitroanilines, dinitrophenols, diphenyl ethers, diphenyl ethers (cbi), glycine derivatives, halogenated alkanoic acids, hydroxybenzonitriles, imidazolinones, isoxazoles, isoxazolidinones, N-phenylphthalimides, organoarsenics, oxadiazoles, oxazolidinediones, oxyacetamides, phenoxycarboxylic acids, phenyl carbamate herbicides, phenylpyrazole herbicides, phenylpyridazines, phosphinic acids, phosphorodithioates, phthalamates, pyrazole herbicides, pyridazines, pyridazinones (PDS), pyridazinones (PSII), pyridines, pyridinecarboxamides, pyridinecarboxylic acids, pyrimidindiones, pyrimidines, pyrimidinyl-oxybenzoics, pyrimidinyloxybenzoic analogs, quinolinecarboxylic acids, BI class and IV including thiocarbamate, semi-carbazones, sulfonylaminocarbonyl-triazolinones, sulfonylureas, tetrazolinones, thiadiazoles, thiocarbamates, triazoles, triazolinones, triazolopyrimidines, triketones, uracils, ureas, 2,3,6-TBA, 2,4,5-T, 2,4-D, 2,4-D-2-ethylhexyl, 2,4-DB, 2,4-D-dimethylammonium, 2,4-D-isopropyl, 2,4-D-isopropyl, 2,4-D-trolamine (2,4-D-triethanolamine), ACD 10614, ACD 10435, acetochlor, acifluorfen, acifluorfen-sodium, aclonifen, acrolein, AD 67, alachlor, alloxydim-sodium, ametryn, amicarbazone, amidosulfuron, amitrole, ammonium sulfamate, anilofos, asulam, atraton, atrazine, azafenidin, azimsulfuron, aziprotryne, barban, beflubutamid, benazolin, benazolin-ethyl, benfluralin, benfuresate, benoxacor, bensulfuron-methyl, bensulide, bentazone, benzobicyclon, benzofenap, benzoylprop, enzoylprop-ethyl, bifenox, bilanafos-sodium, bispyribac-sodium, borax, bromacil, bromobutide, bromofenoxim, bromoxynil, bromoxynil octanoate, bromoxynil-potassium, brompyrazon, butachlor, butafenacil, butenachlor, buthidazole, butralin, butroxydim, buturon, cafenstrole, calcium cyanamide, carbetamide, carfentrazone-ethyl, chlomethoxyfen, chloramben, chlorbromuron, chlorbufam, chlorfenac, chlorfenac-sodium, chlorfenprop, chlorfenprop-methyl, chlorfenprop, chlorfenprop-ethyl, chlorflurenol-methyl, chloridazon, chlorimuron-ethyl, chlornitrofen, chloroacetic acid, chloro-toluron, chloroxuron, chlorpropham, chlorsulfuron, chlorthal-dimethyl, chlorthiamid, cinidon-ethyl, cinosulfuron, clethodim, sethoxydim, tepraloxydim, tralkoxydim, clodinafop-propargyl, clofop, clofop-isobutyl, clomazone, clomeprop, clopyralid, cloquintocet-mexyl, cloransulam-methyl, credazine, cumyluron, cyanamide, cyanazine, cyclosulfamuron, cycloxydim, cycluron, cyhalofop-butyl, cyometrinil, daimuron, dazomet, desmedipham, desmetryn, di-allate, dicamba, dichlobenil, dichlormid, dichlorprop, dichlorprop-isoctyl, dichlorprop-P, diclofop, diclofop-methyl, diclosulam, diethatyl-ethyl; diethatyl, difenoxuron, difenzoquat metilsulfate, diflufenican, diflufenzopyr, dikegulac, dikegulac-sodium, dimefuron, dimepiperate, dimethachlor, dimethametryn, dimethipin, dimethylarsinic acid, dinitramine dinoseb, dinoseb acetate, dinoterb, diphenamid, dipropetryn, disul, disul-sodium, dithiopyr, diuron, DNOC, DSMA, eglinazine-ethyl, eglinazine, EL 177, endothal, ethalfluralin, ethametsulfuron-methyl, ethidimuron, ethofumesate, ethoxysulfuron, etobenzanid, fenchlorazole-ethyl, fenclorim, fenoprop, fenoprop-butotyl, fenoxaprop-ethyl, fenoxaprop, fenoxaprop-P, fenoxaprop-P-ethyl, fenthiaprop, fenthiaprop-ethyl, fentrazamide, fenuron, flamprop-methyl, flamprop-isopropyl, flamprop, flamprop-M-isopropyl, flamprop-M-methyl, flazasulfuron, florasulam, fluazifop-butyl, fluazifop-P, fluazifop-P-butyl, fluazolate, flucarbazone-sodium, fluchloralin, flufenacet, flumetsulam, flumiclorac-pentyl, flumioxazin, flumipropyn, fluometuron, fluorodifen, fluoroglycofen-ethyl, fluothiuron, flupoxam, flupropanate-sodium, flupyrsulfuron-methyl-sodium, flurazole, flurenol-butyl, fluridone, flurochloridone, fluroxypyr, fluroxypyr-meptyl, flurtamone, fluthiacet-methyl, fomesafen, foramsulfuron, fosamine-ammonium, furilazole, glufosinate-ammonium, glyphosate, glyphosate-ammonium, glyphosate-isopropylammonium, glyphosate-sodium, glyphosate-trimesium, halosulfuron-methyl, haloxyfop, haloxyfop-etotyl, haloxyfop-P, hexaflurate, hexazinone, imazamethabenzmethyl, imazamox, imazapic, imazapyr, imazapyr-isopropylammonium, imazaquin, imazethapyr, imazosulfuron, indanofan, iodosulfuron-methyl-sodium, ioxynil, ioxynil octanoate, ioxynil-sodium, isocarbamid, isocil, isomethiozin, isonoruron, isoproturon, isouron, isoxaben, isoxaflutole, isoxapyrifop, karbutilate, lactofen, lenacil, linuron, LS830556, maleic hydrazide, MCPA, MCPA-thioethyl, MCPB, MCPB-ethyl, mecoprop, mecoprop-P, medinoterb acetate, medinoterb, mefenacet, mefenpyrdiethyl, mefluidide, mesosulfuron-methyl, mesotrione, metamifop, metamitron, metazachlor, methabenzthiazuron, methazole, methiuron, methoprotryne, methoxyphenone, methyl isothiocyanate, methylarsonic acid, methyldymron, metobenzuron, metobromuron, metolachlor, metosulam, metoxuron, metribuzin, metsulfuron-, ethyl, MK-616, monalide, monolinuron, monuron, monuron-TCA, MSMA, naphthalic anhydride, naproanilide, napropamide, naptalam, NC-330, neburon, nicosulfuron, nitralin, nitrofen, nonanoic acid, norflurazon, oleic acid (fatty acids), orbencarb, oryzalin, oxabetrinil, oxadiargyl, oxadiazon, oxasulfuron, oxaziclomefone, oxyfluorfen, pendimethalin, penoxsulam, pentachlorophenol, pentanochlor, pentoxazone, perfluidone, pethoxamid, phenisopham, phenmedipham, phenylmercury acetate, picolinafen, primisulfuron-methyl, prodiamine, profluralin, proglinazine-ethyl, proglinazine, prometon, prometryn, propachlor, propanil, propaquizafop, propazine, propham, propisochlor, propoxycarbazone-sodium, propyzamide, prosulfuron, pyraflufen-ethyl, pyrazolynate, pyrazosulfuron-ethyl, pyrazoxyfen, pyribenzoxim, pyributicarb, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sebuthylazine, secbumeton, siduron, simazine, simetryn, S-metolachlor, SMY 1500, sodium chlorate, sulcotrione, sulfentrazone, sulfometuron-methyl, sulfosulfuron, tebuthiuron, tepraloxydim, terbacil, terbumeton, terbuthylazine, terbutryn, thenylchlor, thiazafluron, thiazopyr, thidiazimin, thifensulfuron-methyl, thiobencarb, 1-dichloroacetylazepane, tralkoxydim, tri-allat, triasulfuron, tribenuron-methyl, trichloroacetic acid, triclopyr, tridiphane, trietazine, trifloxysulfuron-sodium, trifluralin, and triflusulfuron-methyl.

Fungicides may include, but are not limited to, amino acid amide carbamates, anilinopyrimidines, antibiotics, aromatic hydrocarbons, heteroaromatics, chloro/nitrophenyls, benzamides (F), benzenesulfonamides, benzimidazoles, benzimidazole precursors, benzotriazines, carboxamides, cinnamic acids, cyanoacetamide oximes, dicarboximides, dithiolanes, DMI: imidazoles, piperazines, pyrimidines, and triazoles; enopyranuronic acid antibiotics, heteroaromatic hydroxyanilides, MBI: dehydratases and reductases; morpholine morpholines, morpholine spiroketalamines, multi-site chloronitriles, multi-site dimethyldithiocarbamates, multi-site guanidines, multi-site inorganics, multi-site phthalimides, multi-site quinones, multi-site sulfamides, N-phenyl carbamate fungicides, organotin fungicides, phenylamide: acylalanines, phenylamide: butyrolactones, phenylamide: oxazolidinones, phenylpyrroles, phenylurea fungicides, phosphonates, phosphorothiolates, pyridazinone fungicides, pyrimidinamines, pyrimidinols, Qil, quinolines, SBI class IV: thiocarbamates, strobilurin analog: dihydrodioxazines, strobilurin type: imidazolinones, strobilurin type: methoxyacrylates, strobilurin type: ethoxycarbamates, strobilurin type: oxazolidinediones, strobilurin type: oximinoacetamides, strobilurin type: oximinoacetates, thiazolecarboxamides, thiocarbamate fungicides, and thiophenecarboxamides. Suitable fungicides include 1,2-dichloro-propane, 2-methoxyethylmercury chloride, 2-phenylphenol, 8-hydroxy-quinoline sulfate, ampropylfos, anilazine, azaconazole, azoxystrobin, benalaxyl, benodanil, benomyl, benquinox, benthiavalicarb-isopropyl, binapacryl, biphenyl, bis (tributyltin) oxide, bitertanol, blasticidin-S, borax, boscalid, bromuconazole, bupirimate, buthiobate, captafol, captan, carbendazim, carboxin, carpropamid, CGA 80 000, chinomethionat, chlobenthiazone, chloraniformethan, chloroneb, chlorothalonil, chlozolinate, climbazole, copper oxychloride, copper sulfate, copper sulfate (tribasic), cuprous oxide, cyazofamid, cyflufenamid, cymoxanil, cyproconazole, cyprodinil, cyprofuram, dazomet, dichlofluanid, dichlone, dichlorophen, diclobutrazol, diclocymet, diclomezine, dicloran, diethofencarb, difenoconazole, difenzoquat metilsulfate, diflumetorim, dimethirimol, dimethomorph, dimoxystrobin, diniconazole, dinobuton, dinocap, diphenylamine, ditalimfos, dithianon, dodemorph, dodemorph acetate, dodine, drazoxolon, edifenphos, epoxiconazole, etaconazole, etem, ethaboxam, ethirimol, etridiazole, famoxadone, fenamidone, fenarimol, fenbuconazole, fenfuram, fenhexamid, fenitropan, fenoxanil, fenpiclonil, fenpropimorph, fentin acetate, fentin hydroxide, ferimzone, fluazinam, fludioxonil, flumorph, fluoroimide, fluotrimazole, fluoxastrobin, fluquinconazole, flusilazole, flusulfamide, flutolanil, flutriafol, folpet, fosetyl-aluminum, fuberidazole, furalaxyl, furametpyr, furconazole-cis, furmecyclox, glyodin, griseofulvin, halacrinate, hexachlorobenzene, hexaconazole, hymexazol, imazalil, imibenconazole, iminoctadine triacetate, iminoctadine tris(albesilate), ipconazole, iprodione, iprovalicarb, isoprothiolane, kasugamycin hydrochloride hydrate, kresoxim-methyl, mebenil, mepanipyrim, mepronil, mercuric chloride, metalaxyl, metalaxyl-M, metconazole, methasulfocarb, methfuroxam, methyl iodide, methyl isothiocyanate, metominostrobin, metsulfovax, mildiomycin, myclobutanil, myclozolin, natamycin, nitrothal-isopropyl, nuarimol, ofurace, oleic acid, fatty acids), oxabetrinil, oxadixyl, oxpoconazole fumarate, oxycarboxin, penconazole, pencycuron, pentachlorophenol, phenylmercury acetate, phenylmercury dimethyldithiocarbamate, phenylmercury nitrate, phosphonic acid, phthalide, picoxystrobin, polyoxin B, polyoxorim, potassium bicarbonate, potassium hydroxyquinoline sulfate, prochloraz, procymidone, propamocarb hydrochloride, propiconazole, proquinazid, prothiocarb; prothiocarb hydrochloride, prothioconazole, pyracarbolid, pyraclostrobin, pyrazophos, pyributicarb, pyrimethanil, pyroquilon, quinoclamine, quinoxyfen, quintozene, silthiofam, simeconazole, sodium bicarbonate, spiroxamine, SSF-109, sulfur, tebuconazole, tecnazene, tetraconazole, thiabendazole, thicyofen, thifluzamide, thiophanate, thiophanate-methyl, thiram, tiadinil, tolclofos-methyl, tolylfluanid, triadimefon, triadimenol, triamiphos, triazoxide, trichlamide, tricyclazole, trifloxystrobin, triflumizole, triforine, triticonazole, urbacid, validamycin, vinclozolin, zarilamid, ziram, and zoxamide.

Bactericides may include, but are not limited to, bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides, acaricides and nematicides may include, but are not limited to, abamectin, ABG-9008, acephate, acequinocyl, acetamiprid, acetoprole, acrinathrin, AKD-1022, AKD-3059, AKD-3088, alanycarb, aldicarb, aldoxycarb, allethrin, alpha-cypermethrin (alphamethrin), amidoflumet, aminocarb, amitraz, avermectin, AZ-60541, azadirachtin, azamethiphos, azinphos-methyl, azinphos-ethyl, azocyclotin, *Bacillus firmus, Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, *Bacillus thuringiensis* israelensis, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin-5-cyclopentyl isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlorantraniliprole, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cisresmethrin, cis-permethrin, clocythrin, cloethocarb, clofentezine, clothianidin, clothiazoben, codlemone, coumaphos, cyanofenphos, cyanophos, cyantraniliprole, cycloprene, cycloprothrin, cyfluthrin, cyflumetofen, cyhalothrin, cyhexatin, cypermethrin, cyphenothrin (1R-trans-isomer), cyromazine, DDT, deltamethrin, demeton-5-methyl, demeton-5-methylsulfone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethion, ethiprole, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubendiamide, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, *Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyrafluprole, pyresmethrin, pyrethrum, pyridaben, pyridalyl, pyridaphenthion, pyridathion, pyrimidifen, pyriprole, pyriproxyfen, quinalphos, resmethrin, RH-5849, ribavirin, RU-12457, RU-15525, rynaxapyr, S-421, S-1833, salithion, sebufos, SI-0009, silafluofen, spinosad, spirodiclofen, spiromesifen, sulfluramid, sulfotep, sulprofos, SZI-121, taufluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027, yl-5201, yl-5301, yl-5302, XMC, xylylcarb, ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3-.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and also preparations which comprise insecticidally active plant extracts, nematodes, fungi or viruses.

As used herein, "plant growing environment" refers to the area where a plant is growing, such as soil in a field or soil containing pots.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

As used herein, "% wt/wt" refers to the percent weight of the material in relation to the percent weight of the formulation.

The following examples are intended to illustrate the present invention and to teach one of ordinary skill in the art how to make the formulations of the invention. They are not intended to be limiting in any way.

EXAMPLES

The following products were the sources of the materials used in the examples.

Agrimer™ VA-6 (available from Ashland) was used as the source of the binder and is a copolymer of acetic acid ethenyl ester and 1-ethenyl-2-pyrrolidinone.

Tween™ 20 (available from Croda) was used as the source of the surfactant and is polyoxyethylene (20) sorbitan monolaurate.

Polyethylene glycol 200 was used as the solvent and is available from Oxiteno, BASF, and Dow.

Zeolex® 7A (Zeolex is available from and a registered trademark of J.M. Huber Corporation) was used as the source of sodium aluminosilicate free flow agent.

Silica sand size range of from about 14 to about 30 mesh (available from Agsco Corporation) was used as the source of the carrier (grains were from about 0.6 to about 1.4 mm in diameter).

Applicant used $GA_3$ in the form of Technical Grade Active Ingredient ("TGAI") when preparing formulations of the present invention. The percent $GA_3$ was about 96.6% w/w. Variations in the amount of $GA_3$ in the TGAI can be accounted for by decreasing or increasing the amount of solvent in order to produce the desired percent of $GA_3$ in the formulation. This is standard practice within the guidelines of U.S. Environmental Protection Agency per 40 C.F.R. §158.175(b)(2).

Example 1

First, a concentrated $GA_3$ formulation was prepared using the amounts indicated below in Table 1 and using the following process. The solvent was warmed in a 3 liter glass beaker with a stir/hot plate. The surfactant was added and mixed. Then the $GA_3$ TGAI t was added and mixed until solubilized. The binder was added and stirred until solubilized. Next, the dye was added and stirred until the formulation was homogenous. The formulation was allowed to cool and then packaged.

FD&C Red #40 was used as the source of the dye in this formulation.

TABLE 1

| Material | % wt/wt | g/batch | Purpose |
| --- | --- | --- | --- |
| $GA_3$ TGAI (96.6% pure) | 10.59 | 160.5 | Active Ingredient |
| PEG 200 | 84.5 | 1279.5 | Solvent |
| Polyoxyethylene (20) sorbitan monolaurate | 1.0 | 15 | Surfactant |
| Copolymer of acetic acid ethenyl ester and 1-ethenyl-2-pyrrolidinone | 2.0 | 30 | Binder |
| Dye | 2.0 | 30 | Color additive |
| Total | 100 | 1515 | |

Next, the 10% $GA_3$ formulation was used to prepare $GA_3$ sand granules using the amounts indicated below in Table 2 and using the following process. The silica sand was put into an electric cement mixer. While blending, the concentrated $GA_3$ formulation was slowly sprayed onto the sand. Then a mixture of $GA_3$ and sodium aluminosilicate was added and blended. Next, the remaining sodium aluminosilicate was added and blended. Finally, the $GA_3$ sand granules were sieved to remove particles larger than 12 mesh and fines less than 30 mesh.

TABLE 2

| Material | % wt/wt | Purpose |
| --- | --- | --- |
| Silica sand | 98.9 | Carrier |
| 10% $GA_3$ formulation from Table 1 | 0.55 | Active ingredient + Solvent + Surfactant + Binder + Dye |
| $GA_3$ TGAI (96.6% pure) + Sodium aluminosilicate mixture | 0.17 0.20 | Active ingredient + Free flow agent |
| Sodium aluminosilicate | 0.25 | Free flow agent |
| Total | 100 | |

Accordingly, a 0.2% $GA_3$ granular formulation was prepared. The sand granules were non-sticky and did not clump together. The formulation appeared homogenous in color and texture and was free flowing.

Example 2

First, a concentrated $GA_3$ formulation was prepared using the amounts indicated below in Table 3 and using the following process. The solvent was warmed in a 3 liter glass beaker with a stir/hot plate. Then the $GA_3$ TGAI and surfactant were added and mixed until solubilized. The binder was added and stirred until solubilized. Next, the dye was added and stirred until the formulation was homogenous. The formulation was allowed to cool and then packaged.

FD&C Blue #1 was used as the source of the dye in this formulation.

TABLE 3

| Material | % wt/wt | g/batch | Purpose |
| --- | --- | --- | --- |
| $GA_3$ TGAI (96.6% pure) | 10.6 | 107 | Active Ingredient |
| PEG 200 | 84.5 | 853 | Solvent |
| Polyoxyethylene (20) sorbitan monolaurate | 1.0 | 10 | Surfactant |
| Copolymer of acetic acid ethenyl ester and 1-ethenyl-2-pyrrolidinone | 2.0 | 20 | Binder |
| Dye | 2.0 | 20 | Color additive |
| Total | 100 | 1010 | |

Next, the 10% $GA_3$ formulation was used to prepare $GA_3$ sand granules using the amounts indicated below in Table 4 and using the following process. The silica sand was put into an electric cement mixer. While blending, the concentrated $GA_3$ formulation was slowly sprayed onto the sand. Then a mixture of $GA_3$ and sodium aluminosilicate was added and blended. Next, the remaining sodium aluminosilicate was added and blended. Finally, the $GA_3$ sand granules were sieved to remove particles larger than 12 mesh and fines less than 30 mesh.

TABLE 4

| Material | % wt/wt | Purpose |
| --- | --- | --- |
| Silica sand | 98.91 | Carrier |
| 10% $GA_3$ formulation | 0.55 | Active ingredient + |

TABLE 4-continued

| Material | % wt/wt | Purpose |
|---|---|---|
| from Table 1 | | Solvent + Surfactant + Binder + Dye |
| GA$_3$ TGAI (96.6% pure) + Sodium aluminosilicate mixture | 0.09 0.20 | Active ingredient + Free flow agent |
| Sodium aluminosilicate | 0.25 | Free flow agent |
| Total | 100 | |

Accordingly, a 0.1% GA$_3$ sand granule formulation was prepared. The sand granules were not sticky and did not clump together. They appeared homogenous in color and texture and were free flowing.

Example 3

The following experiment was conducted to determine the effect of GA$_3$ sand granule formulations of the present invention on rice grain yield. Multiple trials were conducted at Haryana, Uttarakhand, and West Bengal, India. Three GA$_3$ formulations were prepared. Specifically, the sand granule formulation of Table 4 was prepared at both 0.1% and 0.2% GA$_3$ concentrations and 90% technical grade GA$_3$ was prepared as a wettable powder. The GA3 formulations were then diluted and applied as a broadcast spray at a rate of 12.5 grams of active ingredient per hectare along with 50 kilograms per hectare urea. Control rice paddies were treated with urea alone at each location. Rice crop yield was determined between 9 and 18 days after transplanting by calculating the number of earheads per square meter, the number of grains per panicle and 1,000 grain weight. Results of these trials can be seen below in Table 5.

TABLE 5

| Treatment | GA$_3$ Concentration (% wt/wt) | Rate (g/HA) | Yield (Kg/HA) | % Increase |
|---|---|---|---|---|
| Haryana (Average of 4 Trials) | | | | |
| Control | — | — | 5,751 | 0 |
| GA$_3$ Granules | 0.10% | 12.5 | 6,113 | 6.69 |
| GA$_3$ Granules | 0.20% | 12.5 | 6,103 | 6.39 |
| GA$_3$ Wettable Powder | 90% | 12.5 | 6,099 | 6.2 |
| Uttarakhand (Average of 3 Trials) | | | | |
| Control | — | — | 6,710 | 0 |
| GA$_3$ Granules | 0.10% | 12.5 | 7,168 | 6.83 |
| GA$_3$ Granules | 0.20% | 12.5 | 7,248 | 8.01 |
| GA$_3$ Wettable Powder | 90% | 12.5 | 7,181 | 7.02 |
| West Bengal (Average of 2 Trials) | | | | |
| Control | — | — | 3,727 | 0 |
| GA$_3$ Granules | 0.10% | 12.5 | 4,054 | 9.33 |
| GA$_3$ Granules | 0.20% | 12.5 | 4,169 | 12.03 |
| GA$_3$ Wettable Powder | 90% | 12.5 | 4,205 | 13.46 | g/HA denotes grams per hectare
Kg/HA denotes kilograms per hectare

As shown in Table 5, application of 0.1% GA$_3$ sand granule formulation exhibited from 6.69 to 9.33% yield increase in grain. Application of the 0.2% GA$_3$ sand granule formulation exhibited a similar increase from 6.39 to 12.03%. This increase in rice grain yield was similar to that following application of 90% technical grade GA$_3$ wettable powder, which demonstrated a 6.2 to 13.45% increase in rice grain yield.

Example 4

The following experiment was conducted to determine the effect of GA$_3$ sand granule formulations of the present invention on corn seed yield. Multiple trials were conducted at Maharashtra and West Bengal, India. Three GA$_3$ formulations were prepared. Specifically, the sand granule formulation of Table 4 was prepared at both 0.1% and 0.2% GA$_3$ concentrations and 90% technical grade GA$_3$ was prepared as a wettable powder. The GA3 formulations were then diluted and applied as a broadcast spray at a rate of 25 grams of active ingredient per hectare along with urea. Control corn were treated with urea alone at each location. Corn crop yield was determined at 28 days after application by calculating the cob length, the number of columns per cob, the number of grains per cob and 100 seed weight. Results of these trials can be seen below in Table 6.

TABLE 6

| Treatment | GA$_3$ Concentration (% wt/wt) | Rate (g/HA) | Yield (Kg/HA) | % Increase |
|---|---|---|---|---|
| Maharashtra (Average of 2 Trials) | | | | |
| Control | — | — | 6,845 | 0 |
| GA$_3$ Granules | 0.10% | 25.0 | 7,660 | 11.90 |
| GA$_3$ Granules | 0.20% | 25.0 | 7,515 | 9.79 |
| GA$_3$ Wettable Powder | 90% | 25.0 | 7,379 | 7.79 |
| West Bengal (Average of 3 Trials) | | | | |
| Control | — | — | 5,430 | 0 |
| GA$_3$ Granules | 0.10% | 12.5 | 5,625 | 3.6 |
| GA$_3$ Granules | 0.20% | 12.5 | 5,664 | 4.3 |
| GA$_3$ Wettable Powder | 90% | 12.5 | 5,625 | 3.6 | g/HA denotes grams per hectare
Kg/HA denotes kilograms per hectare

As shown in Table 6, application of 0.1% GA$_3$ sand granule formulation exhibited from 3.6 to 11.9% yield increase in seed yield. Application of the 0.2% GA$_3$ sand granule formulation exhibited a similar increase from 4.3 to 9.79%. This increase in corn seed yield was superior to that following application of 90% technical grade GA$_3$ wettable powder, which demonstrated a 3.6 to 7.79% increase in corn seed yield.

Example 5

The following experiment was conducted to determine the effect of GA$_3$ sand granule formulations of the present invention on wheat grain yield. Multiple trials were conducted at Uttarakhand, India. Three GA$_3$ formulations were prepared. Specifically, the sand granule formulation of Table 4 was prepared at both 0.1% and 0.2% GA$_3$ concentrations and 90% technical grade GA$_3$ was prepared as a wettable powder. The GA3 formulations were then diluted and applied as a broadcast spray at a rate of 12.5 grams of active ingredient per hectare along with urea. Control wheat was treated with urea alone at each location. Wheat crop yield was determined at 23 days after application by calculating plant height, tiller count, the number of earheads per square meter, grains per earhead and test weight. Results of these trials can be seen below in Table 7.

TABLE 7

| Treatment | GA$_3$ Concentration (% wt/wt) | Rate (g/HA) | Yield (Kg/HA) | % Increase |
|---|---|---|---|---|
| Maharashtra (Average of 2 Trials) | | | | |
| Control | — | — | 4,844 | 0 |
| GA$_3$ Granules | 0.10% | 12.5 | 5,118 | 6.2 |
| GA$_3$ Granules | 0.20% | 12.5 | 5,145 | 6.7 |
| GA$_3$ Wettable Powder | 90% | 12.5 | 5,060 | 4.9 | g/HA denotes grams per hectare
Kg/HA denotes kilograms per hectare

As shown in Table 7, application of 0.1% GA$_3$ sand granule formulation exhibited a 6.2% yield increase in grain yield. Application of the 0.2% GA$_3$ sand granule formulation exhibited a similar increase of 6.7%. This increase in wheat grain yield was superior to that following application of 90% technical grade GA$_3$ wettable powder, which demonstrated a 4.9% increase in wheat grain yield.

I claim:

1. An agricultural granular formulation comprising:
   from about 0.01 to about 1% wt/wt of at least one gibberellin selected from the group consisting of gibberellic acid (GA$_3$), gibberellin$_4$ (GA$_4$), gibberellin$_7$ (GA$_7$) and gibberellin$_{4/7}$ (GA$_{4/7}$);
   from about 0.1 to about 1% wt/wt of at least one solvent selected from the group consisting of polyethylene glycols with average molecular weights of from about 190 to about 420 daltons and C8 to C12 fatty acid dimethylamides;
   from about 0.0001 to about 0.1% wt/wt of a binder;
   from about 0.0001 to about 0.1% wt/wt of a non-ionic surfactant;
   from about 0.01 to about 2% wt/wt of a free-flow agent; and
   from about 97 to about 99.9% wt/wt of sand granules with average diameters of from about 0.05 to about 2 mm, wherein the formulation sinks when applied to standing water.

2. The formulation of claim 1 comprising from about 0.05 to about 0.3% wt/wt of a gibberellin.

3. The formulation of claim 1 wherein the solvent is polyethylene glycols with average molecular weights of from about 190 to about 210 daltons.

4. The formulation of claim 1 wherein the binder is selected from the group consisting of alkylated vinyl pyrrolidone polymers, a copolymer of acetic acid ethenyl ester and 1-ethenyl-2-pyrrolidinone, and a copolymer of polyvinylpyrrolidone and 1-eicodecene.

5. The formulation of claim 4 wherein the binder is a copolymer of acetic acid ethenyl ester and 1-ethenyl-2-pyrrolidinone.

6. The formulation of claim 1 wherein the non-ionic surfactant is selected from the group consisting of polyoxyethylene (20) sorbitan monolaurate and polyoxyethylene (20) sorbitan monooleate.

7. The formulation of claim 1 wherein the non-ionic surfactant is polyoxyethylene (20) sorbitan monolaurate.

8. The formulation of claim 1 wherein the free-flow agent is selected from the group consisting of sodium aluminosilicate, silicon dioxide, calcium carbonate, and magnesium carbonate.

9. The formulation of claim 8 wherein the free-flow agent is sodium aluminosilicate.

10. The formulation of claim 1 wherein the sand granules have average diameters of from about 0.6 to about 1.4 mm.

11. The formulation of claim 1 wherein the sand is silica sand.

12. The formulation of claim 1 wherein the solvent is polyethylene glycols with average molecular weights of from about 190 to about 210 daltons.

13. An agricultural granular formulation comprising:
   from about 0.01 to about 1% wt/wt of gibberellic acid (GA$_3$);
   from about 0.1 to about 1% wt/wt of at least one solvent selected from the group consisting of polyethylene glycols with average molecular weights of from about 190 to about 420 daltons and C8 to C12 fatty acid dimethylamides;
   from about 0.0001 to about 0.1% wt/wt of a copolymer of acetic acid ethenyl ester and 1-ethenyl-2-pyrrolidinone;
   from about 0.0001 to about 0.1% wt/wt of a non-ionic surfactant selected from the group consisting of polyoxyethylene (20) sorbitan monolaurate and polyoxyethylene (20) sorbitan monooleate;
   from about 0.01 to about 2% wt/wt of sodium aluminosilicate; and
   from about 97 to about 99.9% wt/wt of silica sand granules with average diameters of from about 0.6 to about 1.4 mm, wherein the formulation sinks when applied to standing water.

14. The formulation of claim 13 comprising from about 0.1 to about 0.2% wt/wt of GA$_3$.

15. The formulation of claim 13 wherein the non-ionic surfactant is polyoxyethylene (20) sorbitan monolaurate.

16. A method for regulating plant growth comprising treating a plant or plant growing environment with an effective amount of the formulation of claim 1.

17. The method of claim 16 wherein the effective amount is from about 0.1 to about 30 grams of gibberellin per hectare.

18. The method of claim 16 wherein the effective amount is from about 10 to about 25 grams of gibberellin per hectare.

19. The method of claim 16 wherein the plant is selected from the group consisting of rice, cotton, corn, soybeans, sugarcane, wheat and beets.

20. The method of claim 19 wherein the plant is selected from the group consisting of rice, corn and wheat.

* * * * *